United States Patent
Laske et al.

(10) Patent No.: US 7,141,017 B2
(45) Date of Patent: Nov. 28, 2006

(54) VARIABLE EGM FILTERING AND FIXATION PREDICTION

(75) Inventors: Timothy G. Laske, Shoreview, MN (US); Thomas S. Ahern, Coronado, CA (US)

(73) Assignee: Medtronic, Inc., Minneapolis, MN (US)

( * ) Notice: Subject to any disclaimer, the term of this patent is extended or adjusted under 35 U.S.C. 154(b) by 167 days.

(21) Appl. No.: 10/821,451

(22) Filed: Apr. 9, 2004

(65) Prior Publication Data

US 2005/0015116 A1  Jan. 20, 2005

Related U.S. Application Data

(60) Provisional application No. 60/470,833, filed on May 15, 2003.

(51) Int. Cl.
*A61B 5/00* (2006.01)
*A61B 5/04* (2006.01)

(52) U.S. Cl. .................. 600/300; 600/509

(58) Field of Classification Search .......... 600/508, 600/509, 300; 607/2, 4, 5; 128/901, 898
See application file for complete search history.

(56) References Cited

U.S. PATENT DOCUMENTS

| 4,381,786 A | 5/1983 | Duggan |
| 5,913,880 A | 6/1999 | Vonk |
| 6,256,541 B1 * | 7/2001 | Heil et al. .................. 607/123 |
| 6,636,764 B1 * | 10/2003 | Fain et al. ..................... 607/5 |
| 2004/0002743 A1 * | 1/2004 | Park et al. ..................... 607/25 |

FOREIGN PATENT DOCUMENTS

| EP | 1 084 730 A1 | 3/2001 |
| EP | 1084730 A1 * | 3/2001 |

* cited by examiner

*Primary Examiner*—Mark Bockelman
(74) *Attorney, Agent, or Firm*—Daniel G. Chapik; Girma Wolde-Michael

(57) ABSTRACT

An IMD includes a variable sense amplifier that can be adjusted to counteract the variability created in EGM's due to lead maturation. The effects of lead maturation are either predictively assumed or individually assessed on a given patient. The sense amplifier is then adjusted to assure positive identification of desired events and eliminate unwanted events.

3 Claims, 1 Drawing Sheet

VARIABLE EGM FILTERING AND FIXATION PREDICTION

RELATED APPLICATIONS

This application is related to, and claims the benefit of, provisionally-filed U.S. patent application Ser. No. 60/470,833 filed May 15, 2003, and entitled "Variable EGM Filtering and Fixation Prediction", which is incorporated herein by reference in its entirety.

FIELD OF THE INVENTION

The present invention relates to implantable medical devices. More specifically, the present invention relates to a predictive and/or tailored adjustment of sensitivity and bandpass filter characteristics to increase the accuracy of signal analysis from implanted leads.

DESCRIPTION OF THE RELATED ART

Implantable medical devices (IMD), such as pacemakers, cardioverters, defibrillators, recording devices and the like often rely on implanted leads to sense certain parameters (e.g., cardiac depolarization) and, when appropriate, deliver therapy. As the lead is a foreign object introduced against or into tissue, that tissue will often react. Such reactions include, for example, inflammation and the generation of fibrous tissue growth in and around the area of implantation.

Such tissue reaction can affect the performance of the lead. For example, the inflammation and fibrous tissue growth may possibly partially or fully dislodge the lead from its implantation. More commonly, the tissue changes will alter the electrical characteristics of the local tissue and the perceived signals. That is, the tissue changes affect the inherent electrical conduction characteristics, e.g., resistance, conductivity, of the tissue itself, and thus, the data received by the IMD from an otherwise relatively stable signal will vary over time as these tissue changes occur. The change in signals perceived over time due to tissue reaction is referred to as lead maturation.

Lead maturation often begins to occur immediately after implant. That is, the implantation of the lead results in immediate tissue damage or trauma, especially from active fixation leads. As the tissue heals and responds as noted above, the perceived electrical signal will vary. Thus, an electrogram (EGM) generated by the IMD will likewise vary over time. Therefore, even as the physician is implanting the device and the leads, the received signal could be varying.

While some variation may be minor, certain changes in the generated EGM could affect therapy delivery. For example, R—R intervals are monitored to determine possible ventricular tachycardias. An abnormally fast rate will result in the delivery of the appropriate therapy, such as anti-tachy pacing, cardioversion, or defibrillation. In order to accurately and appropriately deliver the therapy, the R—R interval must be appropriately measured.

In some circumstances, sensed T-waves could be misinterpreted by the IMD as R waves. As such, the sensing of T-waves as R waves could lead to a determination of tachycardia when none is actually present. To prevent the inappropriate sensing of T-waves in this manner, the IMD includes a sense amplifier having a band pass filter. The band pass filter selectively monitors a static, predetermined frequency range. For example, R waves typically are sensed in a range of 25–39 hertz. T-waves are typically lower amplitude and slower than 25 hertz, usually around 10 hertz. Thus, a band pass filter allowing sensed events in a range of 25–39 hertz and at an appropriate gain will generally eliminate T-wave activity.

Lead maturation may affect the sensed T-wave activity. As such, the perceived amplitude and frequency of the sensed T-waves could vary over time, possibly leading to a variation in IMD performance, when a static predetermined bandpass range is utilized. Furthermore, the overall EGM variance over time during lead maturation makes it difficult for the implanting physician to determine what the resultant EGM parameters will be, thus potentially affecting the IMD sensing and therapy parameters.

Similarly, atrial oversensing of P-waves (e.g.), far-field sensing, may occur. Appropriate filtering is used to reduce the effect, but would also be subject to the effects of lead maturation.

DETAILED DESCRIPTION

Figure 1:
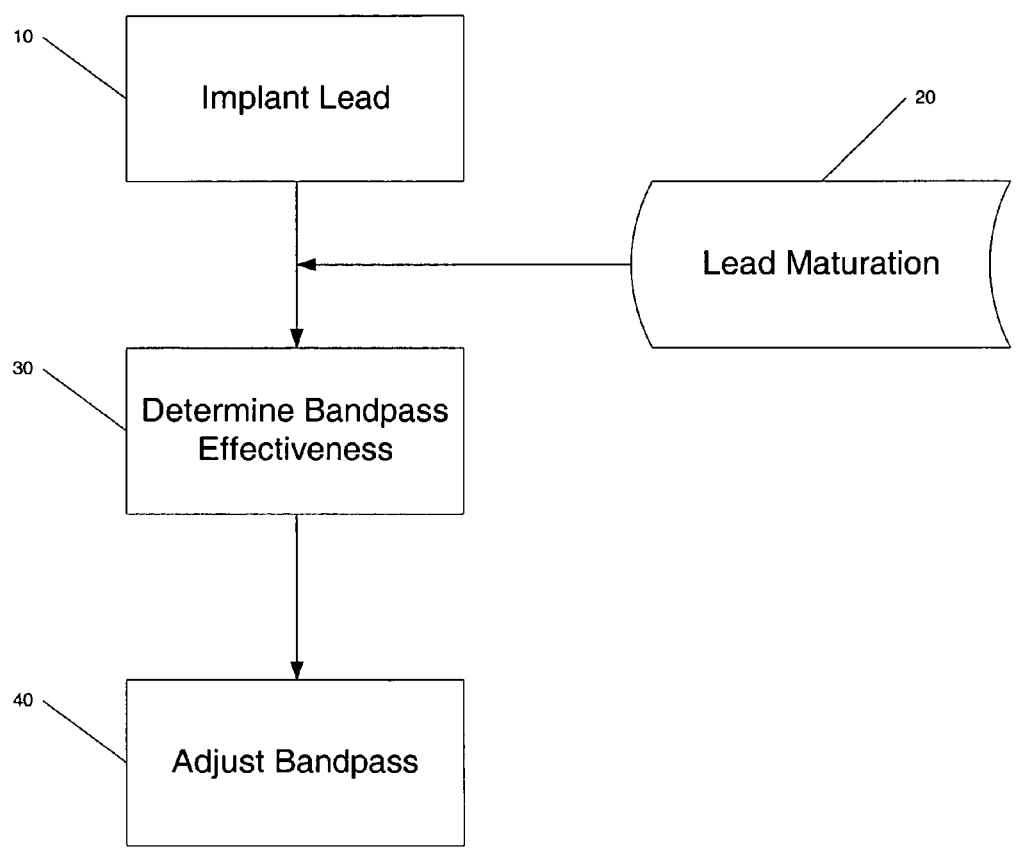
FIG. 1 is a flow chart illustrating the process of determining the proper bandpass range.

In order to account for variations caused by lead maturation, the present invention includes a sense amplifier having a variable range. The range can be altered over time in order to selectively eliminate sensed events that are introduced due to the lead maturation process. For example, if T-wave variance generates improper sensed events because T-wave amplitude has increased or the frequency domain has changed, the gain and/or the bandpass range can be altered either automatically or manually to eliminate the extraneous events. As noted above, typical bandpass ranges are on the order of 25–39 hertz. If T-wave activity is appropriately sensed, the range and sensitivity (gain) can be adjusted to focus on a narrower range, e.g., 30–39 hertz, thereby eliminating the extraneous events. Similarly, adjustments may be made to P-wave sensing parameters in the atrial channel to reduce or eliminate far-field sensing that might occur due to lead maturation.

FIG. 1 illustrates the process of the present invention. At 10, the lead is implanted in the patient and lead maturation 20 begins immediately. The type of lead chosen and its attachment mechanism (e.g., active versus passive) will affect the variance in the lead maturation.

At 30, the process determines the effectiveness of the set IMD parameters in view of the conditions created by lead maturation. One variable so considered would be the range of the bandpass filter utilized in the sense amplifier. Another would be the gain of the same amplifier. If at 30, the process determines that an adjustment is required, that adjustment is made at 40. For example, the bandpass range could be selected to change from a range of 25–39 hertz to a range of 30–39 hertz. Conversely, if lead maturation has not adversely affected the performance of the IMD, then no adjustment is required at 30.

The process of determining 30 the effectiveness of the current parameters, such as the bandpass range can occur in a number of formats. For example, the IMD itself can process the data and determine whether variables should be adjusted. Alternatively, recorded data from a given patient could be analyzed by a physician periodically and the appropriate determinations can be made. Finally, lead maturation can take a predictable form depending upon the type of lead and the affixation method selected. Thus, lead maturation can be predicated on clinical data and a variance in the IMD parameters, e.g., filter bandpass ranges, can be automatically varied over time. That is, variances in the IMD generated EGM due to lead maturation can be predicted and accounted for based on time from implant and the type of lead used.

Whether done on an individual basis by the IMD or the physician or collectively based on predictive clinical data, one method for determining the effectiveness of a given EGM includes the use of a Fast Fourier Transform (FFT). The FFT allows the EGM to be evaluated in the frequency range and to determine stable and predictive frequency bands that allow the events of interest and filter others. The FFT can also be utilized to identify and reject far field waves.

The FFT analysis can also be utilized to asses lead fixation. That is, the absence of a large amplitude, low frequency signal (i.e., injury potential) would predict a higher than normal dislodgement rate.

Additionally, a wavelet or morphology recognition algorithm could be used to analyze the shape and polarity of the T-wave to allow an opportunity for further discrimination of the signal to reduce the likelihood of inappropriate detection as an R-wave.

Although the present invention has been described with reference to preferred embodiments, persons skilled in the art will recognize that changes may be made in form and detail without departing from the spirit and scope of the invention.

The invention claimed is:

1. A method of adjusting an IMD, comprising:
   implanting a lead having an electrode in contact with a sensed medium wherein electrical activity in the sensed medium is sensed by the electrode and representative signals are provided via the lead to the IMD and variations in an electrode-medium interface affect the representative signal;
   determining the effectiveness of selected parameters for a sense amplifier located within the IMD to account for variations in the representative signal generated by variations in the electrode-medium interface; and
   adjusting the selected parameters.

2. A method of adjusting an IMD, comprising:
   implanting a lead;
   determining the effectiveness of selected parameters for a sense amplifier located within the IMD; and
   adjusting the selected parameters, wherein determining the effectiveness includes performing a Fast Fourier Transform of selected data received within the IMD so that the sense amplifier can be adjusted to only include desired events within a given frequency and gain range.

3. The method of claim 1 wherein determining the effectiveness includes the use of a wavelet or morphology recognition algorithm on the selected data received within the IMD so that the sense amplifier can be adjusted to only include desired events within a given frequency and gain range.

* * * * *